US012735618B2

(12) United States Patent
Oshiumi et al.

(10) Patent No.: US 12,735,618 B2
(45) Date of Patent: Sep. 15, 2026

(54) THERMALLY CONDUCTIVE ADDITIVE, THERMALLY CONDUCTIVE COMPOSITE MATERIAL, AND WIRE HARNESS

(71) Applicants: AUTONETWORKS TECHNOLOGIES, LTD., Yokkaichi (JP); SUMITOMO WIRING SYSTEMS, LTD., Yokkaichi (JP); SUMITOMO ELECTRIC INDUSTRIES, LTD., Osaka (JP); KYUSHU UNIVERSITY, NATIONAL UNIVERSITY CORPORATION, Fukuoka (JP)

(72) Inventors: Naoyuki Oshiumi, Yokkaichi (JP); Takehiro Hosokawa, Yokkaichi (JP); Makoto Mizoguchi, Fukuoka (JP)

(73) Assignees: AUTONETWORKS TECHNOLOGIES, LTD., Mie (JP); SUMITOMO WIRING SYSTEMS, LTD., Mie (JP); SUMITOMO ELECTRIC INDUSTRIES, LTD., Osaka (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 675 days.

(21) Appl. No.: 18/029,287

(22) PCT Filed: Oct. 8, 2021

(86) PCT No.: PCT/JP2021/037354
§ 371 (c)(1),
(2) Date: Mar. 29, 2023

(87) PCT Pub. No.: WO2022/085490
PCT Pub. Date: Apr. 28, 2022

(65) Prior Publication Data

US 2023/0365851 A1 Nov. 16, 2023

(30) Foreign Application Priority Data

Oct. 19, 2020 (JP) ................................. 2020-175469

(51) Int. Cl.
*C09K 5/14* (2006.01)
*C07C 49/14* (2006.01)
(Continued)

(52) U.S. Cl.
CPC ................ *C09K 5/14* (2013.01); *C07C 49/14* (2013.01); *C07C 49/213* (2013.01); *C07C 49/78* (2013.01);
(Continued)

(58) Field of Classification Search
CPC .. C09K 5/14; C09C 1/028; C09C 3/08; C08K 5/0091; C08K 9/04; C08K 2201/001;
(Continued)

(56) References Cited

U.S. PATENT DOCUMENTS 4,512,388 A * 4/1985 Claar .................... C09K 5/063 428/404
4,937,310 A 6/1990 Hayashi et al.
(Continued)

FOREIGN PATENT DOCUMENTS

CN 109790026 A 5/2019
CN 110093011 A 8/2019
(Continued)

OTHER PUBLICATIONS

Jan. 11, 2025 Office Action issued in Chinese Patent Application No. 202180070233.7.

(Continued)

*Primary Examiner* — Bijan Ahvazi
(74) *Attorney, Agent, or Firm* — Oliff PLC

(57) ABSTRACT

A thermally conductive additive is excellent in thermal conductivity improvement effect and has high processabil-
(Continued)

[1A]

[1B] [1C]

ity, and a thermally conductive composite material and a wire harness each contain such a thermally conductive additive. The thermally conductive additive includes an organic component and a metal-containing component, where the organic component is configured as an organic compound including a coordination part that can multidentate-coordinate to a metal, and at least one functional group bonded to the coordination part and having a conjugated π-electron system, and the organic component coordinates in the coordination part to a metal atom constituting the metal-containing component to form a coordination complex. The thermally conductive composite material includes the thermally conductive additive and a matrix material, where the thermally conductive additive is dispersed in the matrix material. The wire harness includes the thermally conductive composite material.

13 Claims, 3 Drawing Sheets

(51) Int. Cl.

| | |
|---|---|
| ***C07C 49/213*** | (2006.01) |
| ***C07C 49/78*** | (2006.01) |
| ***C07C 49/825*** | (2006.01) |
| ***C07C 49/83*** | (2006.01) |
| ***C07C 49/84*** | (2006.01) |
| ***C08K 5/00*** | (2006.01) |
| ***C08K 9/04*** | (2006.01) |
| ***C09C 1/02*** | (2006.01) |
| ***C09C 3/08*** | (2006.01) |
| ***H01B 7/00*** | (2006.01) |
| ***H01B 7/42*** | (2006.01) |

(52) U.S. Cl.

CPC ............ *C07C 49/825* (2013.01); *C07C 49/83* (2013.01); *C07C 49/84* (2013.01); *C08K 5/0091* (2013.01); *C08K 9/04* (2013.01); *C09C 1/028* (2013.01); *C09C 3/08* (2013.01); *H01B 7/0045* (2013.01); *H01B 7/421* (2013.01); *C01P 2004/02* (2013.01); *C01P 2004/10* (2013.01); *C01P 2006/32* (2013.01); *C08K 2201/001* (2013.01)

(58) Field of Classification Search

CPC ......... C07C 49/14; C07C 49/78; C07C 49/83; C07C 49/84; C07C 49/213; C07C 49/825; H01B 7/0045; H01B 7/421; C01P 2004/02; C01P 2004/10; C01P 2006/32

See application file for complete search history.

(56) References Cited

U.S. PATENT DOCUMENTS

| | | | | |
|---|---|---|---|---|
| 2004/0102597 | A1 | 5/2004 | Tobita et al. | |
| 2012/0175549 | A1 | 7/2012 | Yoshihara et al. | |
| 2012/0208125 | A1* | 8/2012 | Hatakeyama ......... | G03F 7/0043 430/296 |
| 2014/0076628 | A1* | 3/2014 | McGrath ............. | H01B 7/0045 174/124 R |
| 2020/0048091 | A1 | 2/2020 | Takeda et al. | |

FOREIGN PATENT DOCUMENTS

| | | | | | |
|---|---|---|---|---|---|
| JP | H01-261416 | A | | 10/1989 | |
| JP | 2003-268070 | A | | 9/2003 | |
| JP | 2004-175926 | A | | 6/2004 | |
| JP | 2010-006897 | A | | 1/2010 | |
| JP | 2011-074368 | A | | 4/2011 | |
| JP | 2011-236376 | A | | 11/2011 | |
| JP | 2016-047934 | A | | 4/2016 | |
| JP | 2016056301 | A | * | 4/2016 | .............. C09K 5/06 |
| JP | 2019-116595 | A | | 7/2019 | |

OTHER PUBLICATIONS

Dec. 28, 2021 Search Report issued in International Patent Application No. PCT/JP2021/037354.

* cited by examiner

[1A]

[1B]

[1C]

THERMALLY CONDUCTIVE ADDITIVE, THERMALLY CONDUCTIVE COMPOSITE MATERIAL, AND WIRE HARNESS

TECHNICAL FIELD

The present disclosure relates to a thermally conductive additive, a thermally conductive composite material, and a wire harness.

BACKGROUND ART

In insulating members configuring electrical and electronic components, a thermally conductive additive may be added to an organic polymer material in order to improve heat dissipation and reduce an effect of heat generation due to current application. The thermally conductive additive generally includes thermally conductive filler including particles of an inorganic compound having high thermal conductivity, such as alumina, aluminum nitride, and boron nitride.

When a thermally conductive filler including an inorganic compound is added as the thermally conductive additive to an organic polymer material, particles of the thermally conductive filler need to be brought into close proximity or contact with each other to form a heat conduction path, which means that a larger amount of thermally conductive filler is necessary to be added to obtain sufficient thermal conductivity. In some cases, a large amount of thermally conductive filler, such as 50% by volume or more, needs to be blended into the organic polymer. Adding such a large amount of inorganic compound to the organic polymer may cause problems, such as an adverse effect on properties, including strength, of the organic polymer, an increase in specific gravity, and a reduction in insulation properties, making it difficult to ensure desired high material properties.

On the other hand, a measure other than addition of the thermally conductive filler is also used to increase thermal conductivity of the organic polymer material. For example, there is known a method for improving the thermal conductivity by increasing thermal conductivity of the organic polymer itself or by adding a thermally conductive additive constituted by an organic material to the organic polymer. A method of introducing a rigid and highly oriented site such as a mesogenic group or a liquid crystal structure into a molecule may be used as such a measure for increasing the thermal conductivity of organic molecules. As a specific example, PTL1 discloses, as a thermally conductive resin cured product, an epoxy resin cured product using an epoxy resin monomer having mesogen. PTL2 describes that while a magnetic field is applied in a certain direction to an epoxy resin composition containing a liquid crystalline epoxy resin having a mesogenic group in its molecule, the epoxy resin is cured to produce a thermal conductive epoxy resin molding having a predetermined degree of orientation. PTL3 describes use of a predetermined liquid crystalline thermoplastic resin containing a mesogenic group in its structure as an organic thermally conductive additive to be added when thermal conductivity is added to a plastic. PTL4 and PTL5 each also disclose a resin with liquid crystallinity or a resin into which a mesogenic group has been introduced while no description is given on improvement in thermal conductivity.

CITATION LIST

Patent Literature

PTL1: Japanese Unexamined Patent Application Publication No. 2003-268070.

PTL2: Japanese Unexamined Patent Application Publication No. 2004-175926.

PTL3: Japanese Unexamined Patent Application Publication No. 2016-47934.

PTL4: Japanese Unexamined Patent Application Publication No. Hei 1-261416.

PTL5: Japanese Unexamined Patent Application Publication No. 2010-6897.

SUMMARY OF INVENTION

Technical Problem

As described above, a mesogenic group or a liquid crystalline part is introduced into the organic polymer itself or into an additive including an organic compound to be added to the organic polymer, making it possible to improve thermal conductivity of the organic polymer by using orientation of such a group or site. However, when a highly oriented site such as a mesogenic group is introduced into a molecular structure, processability of the organic polymer or the additive tends to be deteriorated due to an intermolecular interaction associated with orientation of such a site. For example, if a highly oriented site is introduced into a thermoplastic organic polymer, a melting point of the organic polymer becomes higher, and the organic polymer must be heated to a high temperature for molding. In addition, when an additive with high molecular orientation is used, the additive tends to be reduced in solubility in a solvent, or crystal precipitation tends to occur in the additive, which limits use of the additive. The molecular structure of the organic polymer or the additive could be devised to reduce an intermolecular interaction or increase meltability and solubility, but this would result in reduced orientation and increased intermolecular distance, making it difficult to sufficiently increase thermal conductivity.

It is therefore an object to provide a thermally conductive additive excellent in thermal conductivity improvement effect and having high processability, and a thermally conductive composite material and a wire harness, which each contain such a thermally conductive additive.

Solution to Problem

A thermally conductive additive of the disclosure includes an organic component and a metal-containing component, where the organic component is configured as an organic compound including a coordination part that can multidentate-coordinate to a metal, and at least one functional group bonded to the coordination part and having a conjugated Tr-electron system, and the organic component coordinates at the coordination part to a metal atom constituting the metal-containing component to form a coordination complex.

A thermally conductive composite material of the disclosure includes the thermally conductive additive and a matrix material, where the thermally conductive additive is dispersed in the matrix material.

A wire harness of the disclosure includes the thermally conductive composite material.

Advantageous Effects of Invention

The thermally conductive additive according to the disclosure exhibits an excellent thermal conductivity improvement effect and has high processibility. The thermally conductive composite material and the wire harness according to the disclosure each include such a thermally conductive additive.

BRIEF DESCRIPTION OF DRAWINGS

FIG. 1A illustrates a coordination complex in which an organic component coordinates to a metal atom. FIG. 1B illustrates an orientated state where a plurality of coordination complexes is stacked. Each coordination complex is shown in a form of a plane. FIG. 1C shows a state where coordination complexes are formed on the surface of particles of the metal-containing component.

DESCRIPTION OF EMBODIMENTS

Description of Embodiment of the Disclosure

Figure 1:
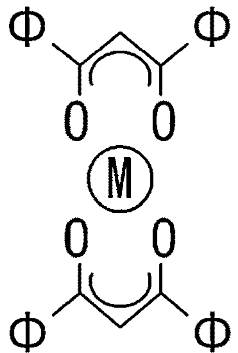
FIGS. 1A to 1C are each a schematic diagram illustrating a structure of a thermally conductive additive according to one embodiment of the disclosure.
Figure 1:
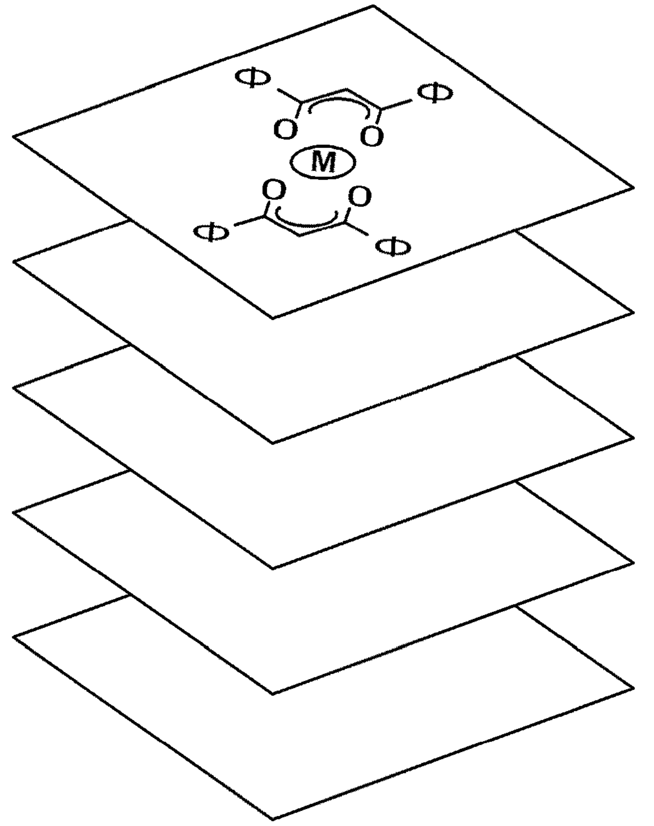
Figure 1:
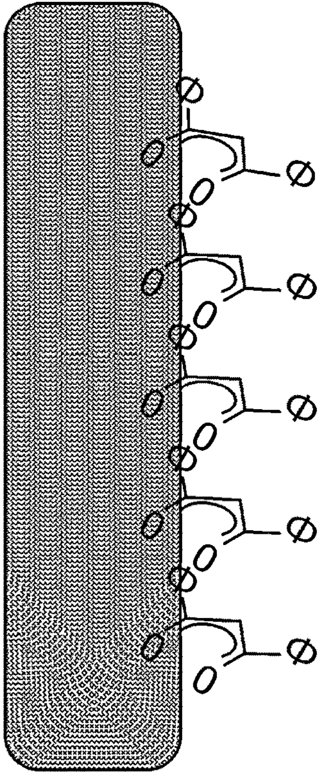

First, some embodiments of the disclosure are listed and explained.

A thermally conductive additive according to the disclosure includes an organic component and a metal-containing component, where the organic component includes a coordination part that can multidentate-coordinate to a metal, and at least one functional group bonded to the coordination part and having a conjugated n-electron system, and the organic component coordinates at the coordination part to a metal atom constituting the metal-containing component to form a coordination complex.

In the thermally conductive additive, conjugated n-electron systems are regularly arranged between a plurality of neighboring complexes due to regularity of the coordination structure of the organic component with respect to a metal atom, or due to regularity of arrangement of metal atoms in the metal-containing component. Thus, π-π interaction may act between the conjugated π-electron systems in neighboring complexes. The π-π interaction aligns orientations of the organic components of the neighboring complexes. As described above, a structure, in which coordination complexes including organic components are oriented with intermolecular interactions, exhibits a high thermal conductivity improvement effect. Thus, adding a thermally conductive additive to a matrix material such as an organic polymer effectively improves thermal conductivity.

In the thermally conductive additive, the organic component coordinates to the metal-containing component to form a coordination complex, and a large number of the coordination complexes are regularly aggregated so that the interaction reversibly acts between the organic components of the neighboring complexes, and strong and irreversible intermolecular interaction does not act in the organic component itself. Hence, the strong and irreversible intermolecular interaction does not cause a reduction in solubility or meltability or an excessive increase in crystallinity. In other words, it is less likely that such phenomena reduce processability or handleability of the thermally conductive additive itself or a composite material, in which the thermally conductive additive is added to a matrix material. In this way, the thermally conductive additive provides excellent thermal conductivity improvement effect and high processability together.

The organic component of the coordination complex preferably performs the interaction at a functional group having the conjugated π-electron system with the organic component of another neighboring complex. In the thermally conductive additive, if the π-π interaction occurs between the coordination complexes, the effect of improving the thermal conductivity due to the π-π interaction can be efficiently provided. If the thermally conductive compound is prepared in advance while the π-π interaction is thus formed between the coordination complexes, the thermally conductive compound can be effectively dispersed in a matrix material such as an organic polymer to achieve a thermal conductivity improvement effect. The formation of the π-π interaction is reversible, and even if the π-π interaction is formed in advance, high processability can be ensured by appropriate heating or the like.

The functional group having the conjugated n-electron system preferably contains an aromatic ring or a condensed aromatic ring system. A functional group containing the aromatic ring or the condensed aromatic ring system is accompanied by strong π-π interaction and tends to be planarly stacked, and thus becomes a thermally conductive additive particularly excellent in thermal conductivity improvement effect.

In this case, the functional group having the conjugated n-electron system preferably contains only one aromatic ring or condensed aromatic ring system. Thus, it is less likely that π-π interaction between the functional groups or orientation excessively increases due to the functional group containing a plurality of aromatic rings or condensed aromatic ring systems, and thus solubility or meltability of the thermally conductive additive is not effectively improved.

The organic component preferably has at least one hydrocarbon group or alkoxy group having 1 to 8 carbon atoms and no conjugated π-electron system, in addition to the functional group having the conjugated π-electron system. Thus, the hydrocarbon group or the alkoxy group having no conjugated π-electron system makes the thermally conductive additive to effectively melt or dissolve in various organic polymers or solvents, leading to a high effect of improving processability.

The coordination part preferably has a β-diketone structure. The β-diketone structure is a structure that can stably bidentate-coordinate to various metal atoms, and effectively has a planar coordination structure. The thermally conductive additive exhibits a high thermal conductivity improvement effect due to the π-π interaction between the planar coordination complexes and the accompanying formation of stacked orientation. In addition, the β-diketone structure can be bonded to various functional groups, including those having a conjugated π-electron system, making it easy to prepare various thermally conductive additives.

In such a case, the organic component preferably has a structure represented by formula (A).

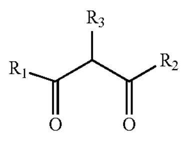

(A)

In the formula, $R_1$ and $R_2$ are each independently a functional group having a conjugated π-electron system, or a hydrocarbon group or an alkoxy group having 1 to 8 carbon atoms and having no conjugated π-electron system, and $R_3$ is a functional group having a conjugated π-electron system, a hydrocarbon group or an alkoxy group having 1 to 8 carbon atoms and having no conjugated π-electron system, or a hydrogen atom, and at least one of the groups $R_1$, $R_2$, and $R_3$ is a functional group having a conjugated π-electron system. The structure also includes a structure in which at least two of the groups $R_1$, $R_2$, and $R_3$ may be connected to each other via a ring structure.

The structure of the above formula (A) has a coordination part including a β-diketone structure, and has, as $R_1$, $R_2$, and $R_3$, a functional group having a conjugated π-electron system, and a hydrocarbon group or an alkoxy group having no conjugated π-electron system and having a relatively small number of carbon atoms, or a hydrogen atom, and is excellent in the balance of thermal conductivity improvement effect based on orientation accompanied by π-π interaction between coordination complexes due to the conjugated π-electron system and high solubility and meltability mainly due to contributions from sites other than the conjugated π-electron system.

The metal-containing component is preferably configured in a form of a fibrous metal compound. Many fibrous metal compounds have high thermal conductivity, and a thermally conductive additive containing such a metal compound is particularly excellent in thermal conductivity improvement effect. The thermally conductive additive can be effectively prepared by coordinating an organic component, which has a coordination part and a functional group having a conjugated π-electron system, to metal atoms on a surface of the fibrous metal compound.

The thermally conductive composite material according to the disclosure includes the thermally conductive additive and a matrix material, where the thermally conductive additive is dispersed in the matrix material.

The thermally conductive composite material contains the described thermally conductive additive according to the embodiment of the disclosure. In the thermally conductive additive, the organic component, which has the coordination part and the functional group having the conjugated π-electron system, and the metal-containing component form a coordination complex, thereby thermal conductivity of the composite material is improved due to orientation of the organic component with π-π interaction between the coordination complexes. Such reversibility of π-π interaction allows the thermally conductive additive to be effectively dissolved or melted in the matrix material. Consequently, even if a thermally conductive additive is added, high processability of the composite material can be ensured.

The matrix material preferably contains an organic polymer. Although many organic polymers have low thermal conductivity, the thermally conductive composite material as a whole can ensure high heat dissipation by adding the thermally conductive additive. The thermally conductive composite material contains an organic component and thus shows high affinity to many organic polymers.

The wire harness according to the disclosure includes the thermally conductive composite material.

The wire harness contains the described thermally conductive composite material, and thus can use the high thermal conductivity and high processability of the thermally conductive composite material. Hence, the wire harness exhibits high heat dissipation, and even if heat generation occurs due to current application to electric wires configuring the wire harness, adverse effect of the heat generation can be reduced. In addition, the wire harness can be effectively manufactured through steps including a step of processing the thermally conductive composite material into a predetermined shape.

Details of Embodiment of the Disclosure

The thermally conductive additive, the thermally conductive composite material, and the wire harness according to the embodiment of the disclosure are described in detail below with reference to the drawings. The thermally conductive composite material of the embodiment of the disclosure includes the thermally conductive additive of the embodiment of the disclosure. The wire harness of the embodiment of the disclosure includes the thermally conductive composite material of the embodiment of the disclosure.

Herein, unless otherwise specified, various physical property values are measured at room temperature in the air. As used herein, a main component of a material means that the relevant component accounts for 50% by mass or more of the mass of all the components that constitute the material. Further, "organic polymer" described herein includes a polymer with a low degree of polymerization, such as oligomer.

<Thermally Conductive Additive>

First, the thermally conductive additive according to one embodiment of the disclosure is described.

(Summary of Composition)

A thermally conductive additive (hereinafter sometimes simply referred to as an additive) according to the embodiment of the disclosure includes an organic component and a metal-containing component. The organic component is configured as an organic compound having a coordination part that can multidentate-coordinate to a metal and at least one functional group bonded to the coordination part and having a conjugated π-electron system. The organic component can be represented by a structure of the following formula (1), where C is the coordination part and F1 is the functional group having the conjugated π-electron system.

F1-C (1)

The functional group F1 may be bonded to the coordination part C directly or through a linking group (excluding those with a conjugated π-electron system). The number of the functional groups F1 bonded to one coordination part C may be one or more, and when there are more than one, those functional groups may be the same as each other or may have different structures each having a conjugated π-electron system. Further, a functional group other than the functional group F1 having the conjugated π-electron system may also be bonded to the coordination part C. The organic component may contain only one or at least two of those represented by formula (1).

The metal-containing component contained in the thermally conductive additive may include only a metal element or may include a metal compound containing a metal element and a non-metal element. From the viewpoint of ease of coordination of the organic component and convenience as the thermally conductive additive, the metal-containing component is preferably a metal compound. Only one type or two or more types of metal-containing component/components may be contained in the thermally conductive additive.

In the thermally conductive additive, the organic component coordinates in a coordination part to a metal atom (including that in an ionic state; the same applies hereinafter) that constitutes the metal-containing component to form a coordination complex. When the metal atom constituting the metal-containing component is denoted as M, the organic component represented by the formula (1) forms the coordination complex represented by the following formula (2).

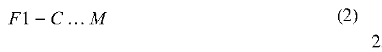

(2)

The dotted line represents a multidentate coordination bond. A plurality of organic components each represented by the formula (1) may be coordinately bonded to one metal atom M. In such a case, the plurality of organic components may have the same structure, or may have different structures, i.e., the functional groups F1, other functional groups, and/or the coordination parts C may have different structures, respectively. Further, the metal atom M may be coordinated with another type of ligand in addition to the organic component as represented by the formula (1).

In the thermally conductive additive according to this embodiment, as described in detail later, when multiple coordination complexes as represented by the formula (2) are adjacent to each other, π-π interaction acts between the functional groups each having the conjugated π-electron system in the organic components of neighboring complexes, resulting in orientation of the functional group. In other words, a plurality of functional groups of the coordination complexes is aligned and take a certain orientation angle. In the thermally conductive additive, the organic component and the metal-containing component may constitute the coordination complex in a state where the thermally conductive additive is used, e.g., after the thermally conductive additive is added to a matrix material such as an organic polymer. Before the thermally conductive additive is used, for example, before being added to the matrix material, the organic component and the metal-containing component may not necessarily constitute the coordination complex and may be independent of each other.

As described above, although the metal-containing component may include only a metal element or a metal compound containing a metal element and a non-metal element, in a state where the organic component coordinates to a metal atom to form a coordination complex, the entire thermally conductive additive containing the coordination complex becomes neutral in charge and takes a solid state. In the solid state, the charge state of the coordination complex is not limited. In other words, in the state where the organic component coordinates to the metal atom, a neutral complex may be formed so that the neutral complex alone forms a solid state. Alternatively, the state where the organic component coordinates to the metal atom may result in formation of a positively charged complex ion that forms a solid state together with a counter ion derived from the non-metallic element in the metal-containing component.

The concrete shape of the metal-containing component in the state where the organic component coordinates to the metal atom is not specified, and may configure a continuum having any appropriate shape such as particles to the extent that the particles can be dispersed in the desired matrix material. Examples of a shape of the particles that can be effectively dispersed in the matrix material include an amorphous granular shape, a fibrous shape, and a rod-like shape. All or some of the metal atoms of the metal-containing component constituting the continuum may be coordinated with the organic component to form the coordination complex. In case of all, the organic component coordinates to the metal atoms occupying the entire area of the continuum of the metal-containing component, such as the particles, and the coordination complex is formed. In case of some, there can be exemplified a mode where the organic component is coordinated only to the metal atoms occupying a surface and the vicinity of the surface of the continuum of the metal-containing component, such as the particles, to form the coordination complex, while the organic component does not coordinate to metal atoms occupying the inner region of the continuum. As described in detail later as a method for manufacturing the thermally conductive additive, the former mode can be preferably formed by a method of forming a coordination complex in a state where the metal-containing component is dissolved or finely dispersed in a solvent, and then obtaining the coordination complex in a solid state by precipitation or the like. The latter mode can be preferably formed by a method of forming a coordination complex by bringing the metal-containing component into contact with a solution containing the organic component while keeping the metal-containing component in a solid state having a predetermined shape. Specifically, in the latter case, the coordination complex is formed on the surface of the particles in which the metal atoms are beforehand arranged into a predetermined structure, which tends to enhance orientation of the organic component due to intermolecular interaction and continuity of the orientation.

(Details of Organic Component)

As described above, the organic component constituting the thermally conductive additive according to this embodiment has, as represented by the formula (1), a structure, in which at least one functional group F1 having the conjugated π-electron system, i.e., having a configuration where carbon-carbon double bonds and single bonds are alternately arranged, as a partial or overall structure of the organic component, is bonded to the coordination part C that can multidentate-coordinate to a metal. Although a specific structure of the organic component is not limited as long as it has the above configuration, a preferred structure of the organic component is described below.

The type of the functional group having the conjugated π-electron system contained in the organic component is not limited and may have a chain portion, a ring portion, or both the chain and ring portions as the conjugated π-electron system. From the viewpoint of stability of the conjugated state or the like, however, the conjugated π-electron system preferably contains the ring structure.

Specifically, the conjugated π-electron system contained in the functional group of the organic component preferably includes an aromatic ring or a condensed aromatic ring system. This is because the aromatic ring and the condensed aromatic ring system are each excellent in stability in a conjugated state, have a planar structure, and can efficiently form a π-π interaction between organic components of neighboring complexes. The aromatic ring contained in the conjugated π-electron system (an aromatic ring contained alone or an aromatic ring constituting a condensed aromatic ring system) may be a benzene ring, or another aromatic ring structure such as a pyrrole ring and a thiophene ring. In the case of the condensed aromatic ring system, multiple types of aromatic rings may be condensed. Preferably, the aromatic ring constituting the conjugated π-electron system is a benzene ring. In other words, the functional group having the conjugated π-electron system is preferably an aryl group or a substituted aryl group. Examples of the aryl group and the substituted aryl group include a phenyl group and a substituted phenyl group, a naphthyl group and a substituted naphthyl group, an anthryl group and a substituted anthryl group, and a phenanthryl group and a substituted phenanthryl group. In the organic component, the phenyl group and the substituted phenyl group, and the naphthyl group and the substituted naphthyl group are particularly preferable from the viewpoint of obtaining an intermolecular interaction of appropriate size. Examples of substituents constituting the substituted aryl group can include, but not limited to, an alkyl group, an alkenyl group, and an alkoxy group. Alternatively, the aryl group may be introduced as a substituent. In such a case, the entire functional group including the conjugated π-electron system has a structure in which multiple (condensed) benzene rings are multimerized through a single bond. The number of carbon atoms in these substituents is preferably 1 to 4 from the viewpoint of securing planarity of the functional group. A substituent such as an alkenyl group may form a conjugated π-electron system continuous with an aromatic ring.

In this embodiment, as described above, the functional group containing the conjugated π-electron system may have a structure in which multiple (condensed) benzene rings are multimerized through single bonds. In such a case, the effect of improving the orientation is also exhibited due to the π-π interaction. However, a structure in which each functional group of the organic component includes only one aromatic ring or condensed aromatic ring system is more preferable than the structure in which multiple (condensed) aromatic rings are contained in one functional group as above. In other words, in a more preferable mode, a single functional group (F1) does not contain multiple aromatic rings that are not condensed with each other. Multiple aromatic rings that are not condensed with each other are allowed not to be contained in a single functional group, making it possible to appropriately control interaction and orientation between organic components of neighboring complexes so as not to be excessively stronger. As will be explained in more detail later, in the thermally conductive additive according to this embodiment, intermolecular interaction to orientate molecules does not work so strongly in the organic component itself, thereby high solubility and meltability are ensured. Hence, intermolecular interaction and orientation in a single functional group are each preferably kept small to some extent. Some functional groups containing multiple aromatic rings that are not condensed to each other are known as mesogenic groups, including a biphenyl group and a phenyl benzoate group. Not limited to them, in this embodiment, the organic component preferably has no mesogenic group. Similarly, from the viewpoint of suppressing intermolecular interactions or orientation to some extent, the organic component preferably contains no hydrogen-bonding substituents, such as an ester group, an amide group, and an imide group, except those included in the coordination part. More preferably, the organic component contains no hydrogen-bonding substituent even in the coordination part.

In the functional group having the conjugated π-electron system, the number of carbon atoms per functional group is preferably four or more, more preferably six or more, from the viewpoint of ensuring interaction between the organic components. On the other hand, the number of carbon atoms per functional group is preferably 24 or less, more preferably 12 or less, from the viewpoint of avoiding an excessive increase in interaction between the organic components. When the organic component has a plurality of functional groups, each having a conjugated π-electron system, in its molecule, the plurality of functional groups with the conjugated π-electron systems may be connected to each other to form a ring structure including a coordination part. When the organic component contains a functional group having no conjugated π-electron system in addition to the functional group having the conjugated π-electron system in the molecule, such two functional groups may be connected to each other.

As described above, the organic component may have the functional group having no conjugated π-electron system in addition to the functional group having a conjugated π-electron system. The organic component includes the functional group having no conjugated π-electron system, which is more effective in appropriately reducing the interaction between molecules of the organic components compared with the case where the organic component includes only the functional group having the conjugated π-electron system. Thus, it is more effective in ensuring the solubility and meltability of the thermally conductive additive. Although a type and a structure of the functional group having no conjugated π-electron system are each not specifically limited, preferred examples thereof include hydrocarbon groups such as an alkyl group and a cycloalkyl group, and an alkoxy group. The number of carbon atoms in each of the functional groups is preferably 1 to 8 from the viewpoint of preventing inhibition of the intermolecular interaction in the functional group having the conjugated π-electron system. The functional group is particularly preferably an alkyl group or an alkoxy group having a carbon number within that range.

The coordination part contained in the organic component is not limited as long as it can multidentate-coordinate to a metal atom, and may coordinate in a bidentate or tridentate or higher manner. In each case, the coordination part can preferably planarly coordinate to a metal atom. Examples of the bidentate coordination part can include those having the respective structures of β-diketone (β-diketonato when coordinated), ethylenediamine, bipyridine, diphosphine, phenanthroline, glycine (glycinato when coordinated), and catechol (catecholato when coordinated). Examples of the tridentate or higher coordination part capable of planar coordination can include macrocyclic structures such as porphyrins, phthalocyanines, and crown ethers. In the macrocyclic structures, the coordination part may not be clearly distinguished from other functional groups. From the viewpoints of the degree of freedom of bonding of functional groups and ease of preparation of the organic component, the coordination part is preferably a bidentate coordination part, and particularly preferably has a β-diketone structure. The β-diketone structure can be stably coordinated planarly to various metal atoms, and can be bonded to various functional groups. The coordination part may have a resonance structure (tautomer), such as an enol structure to the β-diketone structure. Part of the structure of the coordination part may be continuous with the functional group to constitute a conjugated π-electron system.

Preferred examples of the organic component having the β-diketone structure as the coordination part include a molecule as represented by the following formula (A).

(A)

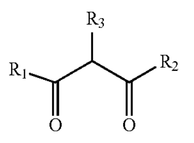

$R_1$ and $R_2$ are each independently a functional group having a conjugated π-electron system or a functional group having no conjugated π-electron system, and R3 is a functional group having a conjugated π-electron system, a functional group having no conjugated π-electron system, or a hydrogen atom, and at least one of the groups of $R_1$, $R_2$, and $R_3$ is a functional group having a conjugated π-electron system. The structure also includes a structure in which at least two of the groups $R_1$, $R_2$, and $R_3$ may be connected to each other via a ring structure. The form, in which a plurality of functional groups are connected via the ring structure, also includes a form, in which carbon atoms constituting the β-diketone structure (C atoms contained in a structure of O═C—C—C═O) are contained in the ring structure formed by the functional groups. In such a case, there is also included a form, in which those ring structures each form a conjugated π-electron system such as an aromatic ring or a condensed aromatic ring system (see HAN in Example) in an enol body generated by resonance of the β-diketone structure.

As described above, $R_1$, $R_2$, and $R_3$ are each selected from either a functional group having a conjugated π-electron system or a functional group having no conjugated π-electron system. $R_3$ may also be a hydrogen atom. However, at least one of the groups of $R_1$, $R_2$, and $R_3$ is a functional group having a conjugated π-electron system. Further, one of the three groups is preferably a functional group having no conjugated π-electron system. The above-described respective relevant functional groups as preferred examples are preferably used as the functional group having the conjugated π-electron system and the functional group having no conjugated π-electron system. Specifically, a functional group having an aromatic ring or a condensed aromatic ring system is preferable as the functional group having the conjugated π-electron system. A hydrocarbon group or an alkoxy group having 1 to 8 carbon atoms is preferable as the functional group having no conjugated π-electron system. A form, in which two out of the three groups of $R_1$, $R_2$, and $R_3$ are functional groups each having a conjugated π-electron system, is particularly preferred. In this form, when two functional groups each having the conjugated π-electron system are not connected to each other, $R_1$ and $R_2$ at two ends are each preferably the functional group having the conjugated π-electron system. On the other hand, when the number of the functional groups each having the conjugated π-electron system is one, $R_3$ in the center is preferably the functional group having the conjugated π-electron system.

(Details of Metal-Containing Components)

As described above, the type of the metal-containing component constituting the thermally conductive additive according to this embodiment is not limited as long as the metal-containing component contains a metal element. The metal-containing component may include only a metal element or may include a metal compound containing a metal element and a nonmetallic element, and preferably includes a metal compound. In the thermally conductive additive, the metal-containing component takes a solid state such as a solid particle state. Examples of preferred metal compounds can include metal hydroxides, metal chlorides, metal carbonates, metal sulfates, metal alkoxides, and the like.

The metal element that constitutes the metal-containing component is also not limited. Examples of preferable metal elements include alkaline earth metals such as Mg and Ca, Al, and Zn. A metal compound containing such a metal element has a relatively high thermal conductivity, and exhibits a high thermal conductivity improvement effect when the metal compound and the organic component are used in a form of the thermally conductive additive. In addition, metal compounds containing these metal elements each have a relatively small specific gravity, and thus effectively provide a thermally conductive additive with a small specific gravity.

The particle shape of the metal-containing component is not limited as long as the metal-containing component can take the solid particle state. Examples of the particle shape can include amorphous powder, a rod shape, a fibrous shape. In particular, the metal-containing component preferably has a highly anisotropic shape, such as the rod shape or the fibrous shape. This is because highly anisotropic metal compound particles often exhibit high thermal conductivity, and when the metal compound particles are coordinated with the organic component to form the thermally conductive additive, the thermally conductive additive also exhibits high thermal conductivity. In particular, the metal compound preferably has the fibrous shape. Examples of the fibrous metal compound exhibiting high thermal conductivity can include basic magnesium sulfate. The metal-containing component preferably, but not limited to, has a particle size (longer axis in case of an anisotropic shape such as the rod shape or fiber shape) of roughly 50 μm or less from the viewpoint of improving the dispersibility in the matrix material.

(Interaction in Coordination Complex)

As described above, in the thermally conductive additive according to this embodiment, the organic component having the conjugated π-electron system multidentate-coordinates in the coordination part to the constituent metal of the metal-containing component to form a coordination complex. The coordination part multidentate-coordinates to the metal in the metal-containing component. Hence, in the coordination complex, the organic component containing the functional group having the conjugated π-electron system is stably bonded to the metal atom in a predetermined positional relationship and angular arrangement compared with a case of monodentate coordination.

FIG. 1A schematically illustrates a structure of a coordination complex with an exemplary case where the coordination part has a β-diketone structure. In the drawing, M represents a metal atom and φ represents a functional group having an aromatic ring or a condensed aromatic ring system. FIG. 1A is shown assuming a case of four coordination.

In the coordination complex, an organic component forms a coordinate bond with a metal atom while being regularly arranged in a predetermined positional relationship. A large number of coordination complexes can form an aggregate while the metal atoms are regularly arranged due to crystallinity of the metal-containing component. In this way, if a large number of coordination complexes, formed by coordination of the organic component to the metal atom, are assembled in a regular arrangement, an attractive interaction may occur between the organic components of neighboring complexes. That is, π-π interaction occurs between the conjugated π-electron systems contained in the organic components of the coordination complexes arranged adjacent to each other. Further, the π-π interaction aligns the organic components of the neighboring complexes in a predetermined direction.

For example, the coordination complex shown in FIG. 1A has a planar structure, and conjugated n electrons are distributed in the vertical direction of the plane of the coordination complex shown as a square plane in FIG. 1B. A π-π interaction acts between the planes of the neighboring complexes. Thus, as shown in FIG. 1B, there is formed a structure, in which neighboring complexes are mutually oriented in a direction of parallel alignment of the planes of the coordination complexes due to attractive interaction acting between the planes, and a large number of coordination complexes are stacked. Alternatively, as shown in FIG. 1C, an organic component coordinates to a metal atom (not shown) on the surface of a solid particulate metal-containing component (shown with hatching) to form a coordination complex, during which π-π interaction acts between adjacently coordinated organic components. The π-π interaction results in a structure in which the organic component is oriented in a specific direction on the surface of the metal-containing component. In FIG. 1C, only one organic component is shown for each coordination complex to simplify representation.

In this way, the functional groups having conjugated π-electron systems, which exert mutual attractive interaction between organic components of multiple coordination complexes and are aligned in orientation in a predetermined direction, form an aggregate and thus suppress phonon scattering and improve thermal conductivity. Such an oriented coordination complex thus serves as the thermally conductive additive, and when mixed with a matrix material such as an organic polymer material, the coordination complex improves thermal conductivity of the material. Although a specific orientation structure of the coordination complex is not limited as long as the orientation is aligned between the coordination complexes, a form of a stacked orientation structure, in which the planes constituting the conjugated π-electron systems are laminated in parallel, is particularly preferred. When the conjugated π-electron system is constituted by an aromatic ring or a condensed aromatic ring system, the stacked oriented structure is effectively formed.

The thermally conductive additive according to this embodiment exhibits the thermal conductivity improvement effect by a structure via relatively weak and reversible intermolecular interactions, i.e., the coordinate bond and the π-π interaction, rather than by the structure within one molecule or by strong or highly irreversible interaction that acts between molecules. Hence, the thermally conductive additive according to this embodiment has excellent solubility insolvents and meltability when heated, and thus provides excellent processability during addition to or mixing/kneading with a matrix material such as organic polymer. In addition, unwanted crystallization is less likely to occur.

In a state where π-π interaction is formed between organic components of neighboring complexes as shown in FIGS. 1B and 1C, when the thermally conductive additive is added to the matrix material and mixed therewith, π-π interaction between the coordination complexes can be effectively reduced or eliminated by appropriate use of a solvent or appropriate heating. If an operation such as mixing or kneading is performed in such a state, it is possible to reduce adverse effect of aggregation of coordination complex due to π-π interaction and facilitate dissolution or melting of the coordination complex. After that, removing of the solvent by volatilization etc., or stop of heating is appropriately performed, π-π interaction can be formed again between the neighboring coordination complexes. Thus, the thermally conductive additive is highly uniformly dispersed in the matrix material, and a state where the thermal conductivity improvement effect is exhibited can be formed by π-π interaction between coordination complexes and the orientation associated with it. In the case where not only the π-π interaction but also the coordinate bond between the organic component and the metal-containing component is eliminated along with dissolution in a solvent or melting by heating, or in the case where the organic component and the metal-containing component are independently added to the matrix material or the solvent and then the coordination complex is formed in the matrix material, the organic component and the metal-containing component constituting the thermally conductive additive can be dissolved or melted with higher solubility or meltability.

An additive or an organic polymer constituted as the organic molecule containing a mesogenic group or a liquid crystal structure as those disclosed in PTL1 to PTL5 can also exhibit the thermal conductivity improvement effect based on suppression of phonon scattering by the intermolecular interaction and the molecular orientation associated with it, as with the thermally conductive additive according to this embodiment. However, when the organic molecule has a mesogenic group or a liquid crystal structure, since strong intermolecular interaction acts, dissolution in a solvent or melting by heating is less likely to occur, and processability may often be deteriorated. Compared with such a case, for the thermally conductive additive according to this embodiment of the disclosure, the thermal conductivity improvement effect is exhibited based on the coordination structure in which the organic component coordinates to the metal-containing component as described above, and thus excellent processability is provided.

(Method for Manufacturing Thermally Conductive Additive)

An exemplary method for manufacturing the above-described thermally conductive additive according to this embodiment of the disclosure is now described. First, the metal-containing component to be used is dissolved together with the organic component in a solvent such as a highly polar solvent, or finely dispersed in a form of fine particles that do not retain the shape of the metal-containing component being a raw material. The organic component is then coordinated to the metal atom of the metal-containing component by mixing the solution while appropriately performing operations such as heating, stirring, and addition of a reactant. Subsequently, the solvent is removed from the prepared reaction liquid by volatilization or the like, and the metal-containing component, which has been formed into a coordination complex through coordination of the organic component, is produced in a solid state by precipitation or the like. Alternatively, the prepared reaction liquid is first dispersed in the matrix material, and then the solvent is removed. Alternatively, as another method for manufacturing the thermally conductive additive, a metal-containing component and an organic component in a state of forming no coordination complex may be appropriately added together with a solvent to a matrix material and dispersed therein to form a coordination complex in the matrix material. In such cases, the composition of the metal-containing component that constitutes the resultant product may be the same as that of the metal-containing component that has been initially used as the raw material, or may become different through a reaction such as coordination.

As described above, according to the method in which an organic component is coordinated to a dissolved or finely dispersed metal-containing component and then the coordination complex is formed in a solid state, or the method in which a coordination complex is formed in a matrix material, the thermally conductive additive is likely to be produced in a state where the coordination complex is formed in substantially the entire area of the solid metal-containing component. Specifically, as illustrated in FIG. 1B, thermally conductive additive particles are likely to be produced in a form of an aggregate in which a large number of coordination complexes are assembled in a predetermined orientation, for example, in a stacked manner, due to the π-π interaction. The manufacturing method, in which the metal-containing component is dissolved or finely dispersed and then the organic component is coordinated as described above, is applied to samples other than those using basic magnesium sulfate inorganic fibers as the metal-containing component in Example as described later.

Alternatively, particles of the metal-containing component are brought into contact with the organic component while maintaining the original particle shape without being dissolved or finely dispersed to eliminate the original particle shape, thereby the thermally conductive additive can also be manufactured. At this time, the organic component may be brought into contact with the metal-containing component while being dissolved in a solvent. However, the solvent needs to be selected so as not to dissolve the metal-containing component. When the metal-containing component is brought into contact with the organic component by such methods, the organic component coordinates to a metal atom on a surface of the particle of the metal-containing component to form a coordination complex, as shown in FIG. 1C. This may result in a state where the organic component is predeterminately oriented due to π-π interaction between adjacently formed coordination complexes. In this way, the manufacturing method, in which the organic component is coordinated while the particle shape of the metal-containing component is maintained, can be preferably used when a sparingly soluble metal-containing component is used, and in the later-described Example, the method is applied to the case where a basic magnesium sulfate inorganic fiber is used as the metal-containing component.

In any case, the fact that the orientation due to π-π interaction is achieved in the resultant coordination complex can be confirmed, for example, by observation using a polarizing microscopy or by infrared absorption spectroscopy (FT-IR) spectrum measurement. For example, when particles of the resultant thermally conductive additive are observed with a polarizing microscope, particles arranged in a specific direction corresponding to the polarized light, or a partial site of one particle are/is observed remarkably brighter than other particles or other sites, which is an index of orientation of the organic component in a predetermined direction. Alternatively, in FT-IR measurement, the wavenumber shifts of an infrared absorption peak derived from the organic component is sometimes associated with the π-π interaction.

<Thermally Conductive Composite Material>

A thermally conductive composite material (hereinafter sometimes simply referred to as a composite material) according to one embodiment of the disclosure is now described. The thermally conductive composite material according to this embodiment includes the above-described thermally conductive additive according to the embodiment of the disclosure and a matrix material. The thermally conductive additive is dispersed in the matrix material.

In the thermally conductive composite material according to this embodiment, adjacent organic components contained in the coordination complexes to constitute the added thermally conductive additive form the π-π interaction therebetween, and furthermore the π-π interaction causes the organic components to be aligned in a predetermined orientation. This orientation causes the thermal conductivity improvement effect to be exhibited, and thus the thermally conductive composite material of the embodiment exhibits high thermal conductivity. Furthermore, in the thermally conductive composite material, when particles of the metal-containing component constituting the thermally conductive additive are appropriately in contact with each other via an organic component, the metal-containing component itself forms a thermally conductive path and functions as a thermally conductive filler, which also improves thermal conductivity of the thermally conductive composite material. However, since the thermally conductive additive contains the organic component, and the thermal conductivity improvement effect due to the π-π interaction in the organic component can be used, a high thermal conductivity improvement effect is provided even if the adding amount of the metal-containing component itself is controlled small compared with a case where only the metal-containing component is used as the thermally conductive filler. As a result, the thermal conductivity can be effectively improved while adverse effects, which may occur when a large amount of metal-containing component is added, are suppressed, the adverse effects including an increase in specific gravity, deterioration of matrix material characteristics such as material strength, and deterioration of insulating properties. The organic component is disposed on the surface of the metal-containing component, which further provides an effect of enhancing affinity between the metal-containing component and the matrix material including an organic material.

Although a type of the matrix material is not limited, the matrix material preferably contains an organic polymer, and more preferably contains an organic polymer as a main component. Specific examples of the organic polymer that constitutes the matrix material include various resins, thermoplastic elastomers, rubbers, and the like. When a resin material is used as the matrix material, the resin material may be a curable resin, a thermoplastic resin, or a solvent-soluble plastic, depending on desired application. Examples of types of the resin constituting the matrix material include olefin resins such as polyethylene and polypropylene, halogen resins such as polyvinyl chloride, polylactic acid, polystyrene resin, polyvinyl acetate, ABS resin, AS resin, acrylic resin, methacrylic resin, polyamide resin, urethane resin, silicone resin, fluorine resin, polyvinyl alcohol, polyimide, polyacetal, polycarbonate, modified polyphenylene ether (PPE), polyethylene terephthalate, polybutylene terephthalate, polyphenylene sulfide, and epoxy resins, and copolymers or polymer alloys of these resins. The matrix material may contain only one type of organic polymer, or may contain a plurality of organic polymers. The matrix material preferably contains no mesogenic group and no liquid crystal structure in its molecular structure. The matrix material may optionally contain an additive such as a flame retardant, filler, and a colorant in addition to the organic polymer. However, an additive having another type of thermal conductivity improvement effect, such as inorganic filler, is preferably not added, except for unavoidable impurities, to the thermally conductive composite material.

In the thermally conductive composite material according to this embodiment, the content of the thermally conductive additive may be appropriately determined such that the thermally conductive composite material as a whole exhibits a desired thermal conductivity. The higher the thermally conductive additive content, the higher the thermal conductivity of the composite material. The content of the thermally conductive additive may be determined such that thermal conductivity of the composite material is, for example, 1.5 times or more, 2.0 times or more, or 2.5 times or more higher than that of the matrix material. Although the thermal conductivity of the thermally conductive composite material is preferably as high as possible, from the viewpoint of avoiding an increase in specific gravity due to excessive addition of the thermally conductive additive, the content of the thermally conductive additive may be determined such that the thermal conductivity of the composite material is, for example, 5 times or less or even 4 times or less of that of the matrix material containing no thermally conductive additive added thereto. Alternatively, the content of the additive may be determined such that the specific gravity of the composite material is 1.5 times or less or even 1.2 times or less of that of the matrix material containing no thermally conductive additive added thereto.

When the content of the thermally conductive additive is defined by the proportion of the additive in the entire thermally conductive composite material, the content of the thermally conductive additive may be roughly 20% by volume or more, or 30% by volume or more from the viewpoint of sufficient improvement in thermal conductivity of the thermally conductive composite material. On the other hand, from the viewpoint of suppressing an increase in specific gravity of the thermally conductive composite material, the content may be 60% by volume or less, or 50% by volume or less.

The thermally conductive composite material according to this embodiment can be manufactured by adding the thermally conductive additive, which is manufactured by the above-described manufacturing method and contains the coordination complex including the metal-containing component and the organic component, to the matrix material at a predetermined blending ratio followed by mixing and kneading. Alternatively, the thermally conductive composite material may be manufactured by dispersing the metal-containing component and the organic component in a state of forming no coordination complex in a matrix material such that the coordination complex is formed in the matrix material. When the thermally conductive composite material containing the coordination complex is dispersed or formed in the matrix material by such methods, since the π-π interaction formed between the organic components and the coordinate bond between the organic component and the metal-containing component are each reversibly formed or eliminated, the coordination complex and the organic component are effectively dispersed in the matrix material, resulting in high processability. At this time, higher processability is achieved by using a solvent or by heating the material. When a solvent is used in the manufacturing process of the thermally conductive composite material, the solvent is preferably removed by heat drying or degassing as appropriate after manufacturing. The manufactured thermally conductive composite material may be used as it is, or may be used after being formed into a desired shape through steps such as melting, dissolving, and curing.

As described above, the thermally conductive composite material according to this embodiment achieves both high thermal conductivity and low specific gravity, and has excellent processability. This thermally conductive composite material therefore can be effectively manufactured and processed to be used as a suitable material to configure a member that requires both lightness and heat dissipation. Although specific application of the thermally conductive composite material is not limited, a case of using the thermally conductive composite material as a component material of a wire harness is exemplified in detail below.

<Wire Harness>

Figure 2:
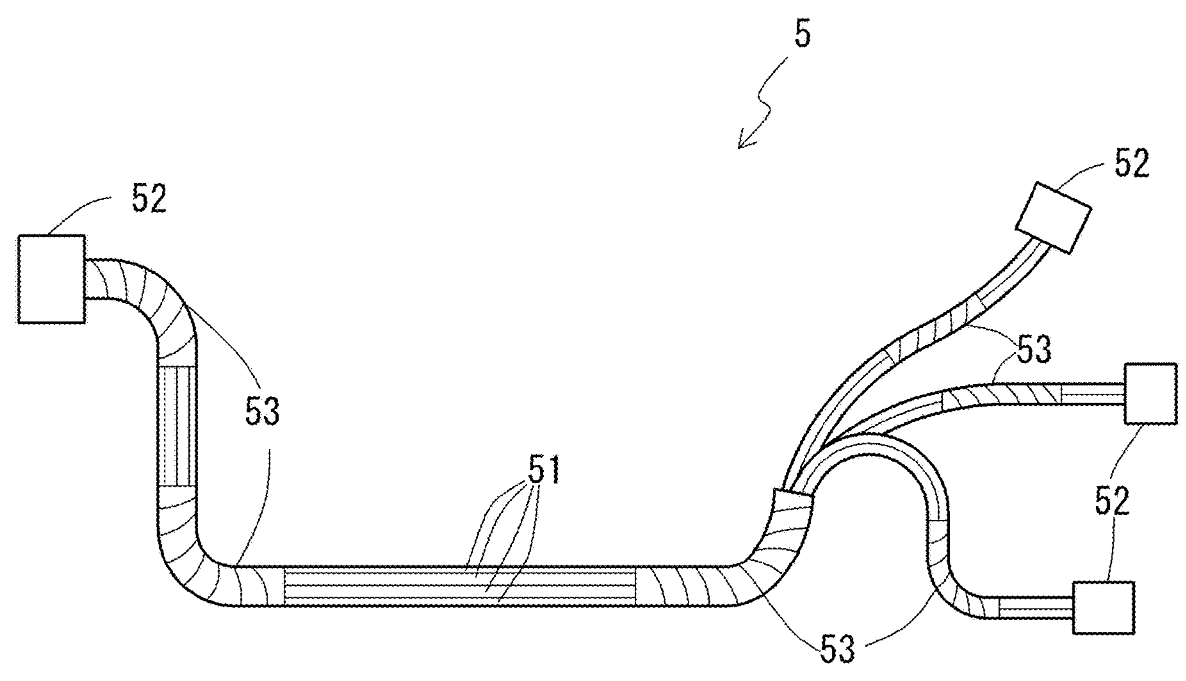
FIG. 2 is a side view illustrating a wire harness according to one embodiment of the disclosure.

Finally, a wire harness according to an embodiment of the disclosure is described. The wire harness of this embodiment includes the thermally conductive composite material according to the embodiment of the disclosure as described above. As illustrated in FIG. 2, a wire harness 5 is provided with connectors 52 each including a connection terminal (not shown) at an end portion of an insulated wire 51 having an insulating coating on the outer circumference of a wire conductor. In the wire harness 5, a plurality of insulated wires 51 may be bundled. In such a case, a tape 53 can be used as an exterior material for bundling the insulated wires 51.

In the wire harness 5 according to this embodiment, the thermally conductive composite material according to the embodiment of the disclosure as described above can configure various members requiring heat dissipation. A thermally conductive composite material, in which the thermally conductive additive is added to the organic polymer as the matrix material, is preferred to be mainly used as a constituent material of the insulating member. Examples of such an insulating member can include an insulating coating to configure the insulated wire 51, an exterior material such as a tape 53 or a protective tube disposed on an outer side of the insulated wire 51, an adhesive used for fixing between component members and for water stoppage, and a connector housing to configure the connector 52. The thermally conductive composite material may be disposed between the protective tube such as a corrugated tube and the insulated wire 51.

Recently, in the field of automobiles, especially in electric vehicles and hybrid vehicles, the amount of heat generated from electric wires tends to increase with an increase in electric current flowing through the electric wires. In addition, a large number of wires and electrical connection members are increasingly disposed in close proximity. In such cases, it is important that the various members configuring the wire harness 5 have high heat dissipation from the viewpoint of minimizing adverse effect of heat dissipation from the electric wires and the electrical connection members. In the wire harness 5, the member that may be affected by such heat dissipation is formed using the thermally conductive composite material having high thermal conductivity, making it possible to efficiently dissipate heat. In the field of automobiles, weight reduction of component members is an important issue, and use of the above-described thermally conductive composite material with a specific gravity controlled to be low can also contribute to weight reduction of the wire harness 5. Further, the high processability of the thermally conductive composite material can be used to effectively manufacture various component members having various shapes and variously disposed.

EXAMPLE

Hereinafter, examples will be described. The present invention is not limited by the Example. In this Example, a thermally conductive additive was prepared so as to contain a coordination complex including an organic component that coordinates to a metal-containing component, and evaluation was made on a state of the thermally conductive additive, and on specific gravity and thermal conductivity of a thermally conductive composite material containing the thermally conductive additive. Hereinafter, unless otherwise specified, samples were prepared and evaluated at room temperature in air.

Test Method (1) Additive Preparation

First, a plurality of additives was prepared as additives each containing a coordination complex with an organic component coordinated to a metal-containing component.

(1-1) Used Organic Component

Listed below are names and abbreviations (indicated by < >), molecular weights (MW), and structural formulas of compounds used as organic components in preparation of the additives. For HBP and HAN, resonance structures are also shown.

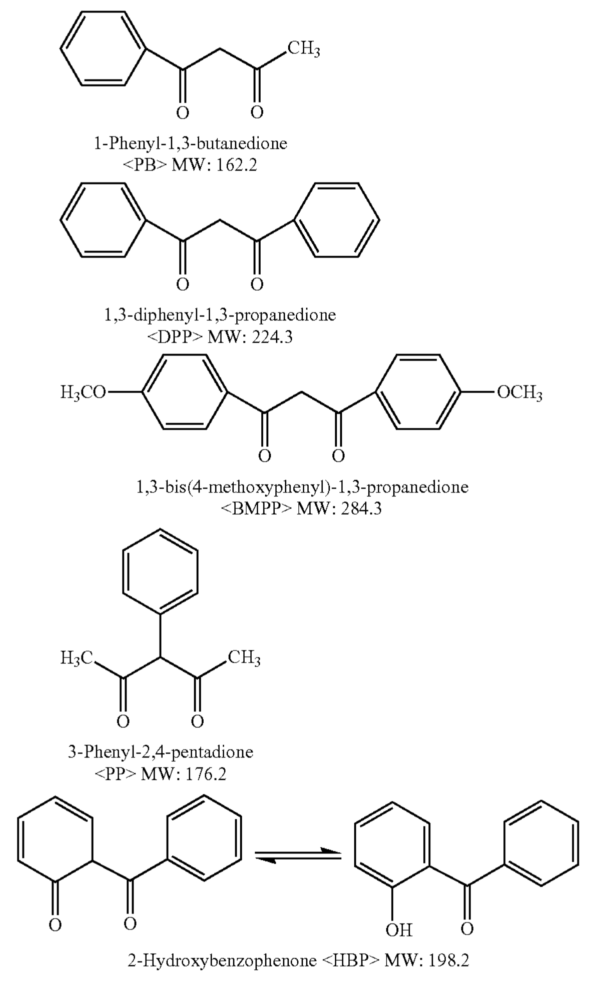

1-Phenyl-1,3-butanedione
<PB> MW: 162.2

1,3-diphenyl-1,3-propanedione
<DPP> MW: 224.3

1,3-bis(4-methoxyphenyl)-1,3-propanedione
<BMPP> MW: 284.3

3-Phenyl-2,4-pentadione
<PP> MW: 176.2

2-Hydroxybenzophenone <HBP> MW: 198.2

-continued

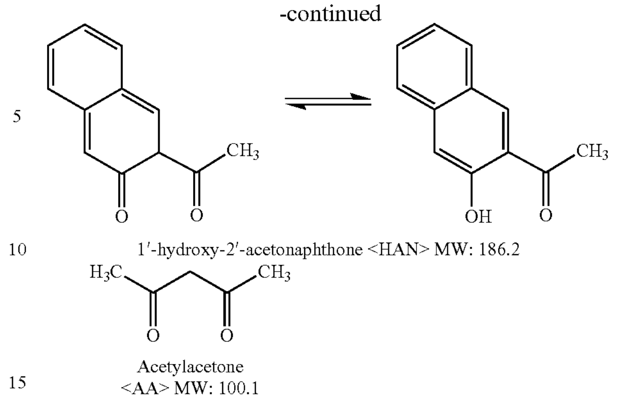

1′-hydroxy-2′-acetonaphthone <HAN> MW: 186.2

Acetylacetone
<AA> MW: 100.1

(1-2) Used Metal-Containing Component

Listed below are names and abbreviations (indicated by < >) of metal compounds used as the metal-containing components in preparation of the additives, and molar contents of the metal elements.

Calcium Methoxide <Ca-MET> (9.8 mmol Ca/g)

Aluminum Isopropoxide <Al-IP> (4.9 mmol Al/g)

Basic Magnesium Carbonate <MgCO3> (10 mmol Mg/g)

Basic Zinc Carbonate <ZnCO3> (9.0 mmol Zn/g)

Basic Magnesium Sulfate Inorganic Fiber <MOS> (13 mmol Mg/g)

(1-3) Additive Preparation Method

The materials listed above were appropriately combined to prepare additives as follows. Names and preparation methods of the additives are listed.

PB—Ca

After 10 g (61.7 mmol) of PB and 3.16 g (31 mmol) of Ca-MET were stirred and homogenized in an isopropanol/methanol solvent for 30 minutes, the solvent was distilled with an evaporator, followed by vacuum drying.

PB—Al

After 10 g (61.7 mmol) of PB and 4.29 g (21 mmol) of Al—IP were stirred and homogenized in an isopropanol/toluene solvent for 30 minutes, the solvent was distilled with an evaporator, followed by vacuum drying.

PB—Mg

After 10 g (61.7 mmol) of PB and 3.10 g (31 mmol) of MgCO3 were stirred and homogenized in an isopropanol/water solvent for 30 minutes, the solvent was distilled with an evaporator, followed by vacuum drying.

PB—Zn

After 10 g (61.7 mmol) of PB and 3.44 g (31 mmol) of ZnCO3 were stirred and homogenized in an isopropanol/water solvent for 30 minutes, the solvent was distilled with an evaporator, followed by vacuum drying.

PB-MOS

After 10 g (61.7 mmol) of PB and 10 g (130 mmol) of MOS were stirred and homogenized in an isopropanol/water solvent for 30 minutes, the solvent was distilled with an evaporator, followed by vacuum drying.

DPP-Al

After 10 g (44.6 mmol) of DPP and 3.04 g (14.9 mmol) of Al—IP were stirred and homogenized in an isopropanol/toluene solvent for 30 minutes, the solvent was distilled with an evaporator, followed by vacuum drying.

DPP-Mg

After 10 g (44.6 mmol) of DPP and 2.23 g (22.3 mmol) of MgCO3 were stirred and homogenized in an isopropanol/water solvent for 30 minutes, the solvent was distilled with an evaporator, followed by vacuum drying.

DPP-MOS

After 10 g (44.6 mmol) of DPP and 10 g (130 mmol) of MOS were stirred and homogenized in an isopropanol/water solvent for 30 minutes, the solvent was distilled with an evaporator, followed by vacuum drying.

BMPP-Mg

After 10 g (35.2 mmol) of BMPP and 1.76 g (17.6 mmol) of MgCO3 were stirred and homogenized in an isopropanol/water solvent for 30 minutes, the solvent was distilled with an evaporator, followed by vacuum drying.

BMPP-MOS

After 10 g (35.2 mmol) of BMPP and 10 g (130 mmol) of MOS were stirred and homogenized in an isopropanol/water solvent for 30 minutes, the solvent was distilled with an evaporator, followed by vacuum drying.

PP—Mg

After 10 g (56.8 mmol) of PP and 2.84 g (28.4 mmol) of MgCO3 were stirred and homogenized in an isopropanol/water solvent for 30 minutes, the solvent was distilled with an evaporator, followed by vacuum drying.

PP-MOS

After 10 g (56.8 mmol) of PP and 10 g (130 mmol) of MOS were stirred and homogenized in an isopropanol/water solvent for 30 minutes, the solvent was distilled with an evaporator, followed by vacuum drying.

HPB—Mg

After 10 g (50.5 mmol) of HPB and 2.53 g (25.3 mmol) of MgCO3 were stirred and homogenized in an isopropanol/water solvent for 30 minutes, the solvent was distilled with an evaporator, followed by vacuum drying.

HPB-MOS

After 10 g (50.5 mmol) of HPB and 10 g (130 mmol) of MOS were stirred and homogenized in an isopropanol/water solvent for 30 minutes, the solvent was distilled with an evaporator, followed by vacuum drying.

HAN-Mg

After 10 g (53.7 mmol) of HAN and 2.69 g (26.9 mmol) of MgCO3 were stirred and homogenized in an isopropanol/water solvent for 30 minutes, the solvent was distilled with an evaporator, followed by vacuum drying.

HAN-MOS

After 10 g (53.7 mmol) of HAN and 10 g (130 mmol) of MOS were stirred and homogenized in an isopropanol/water solvent for 30 minutes, the solvent was distilled with an evaporator, followed by vacuum drying.

AA-Mg

After 10 g (99.9 mmol) of AA and 4.99 g (49.9 mmol) of MgCO3 were stirred and homogenized in an isopropanol/water solvent for 30 minutes, the solvent was distilled with an evaporator, followed by vacuum drying.

AA-MOS

After 10 g (99.9 mmol) of AA and 10 g (130 mmol) of MOS were stirred and homogenized in an isopropanol/water solvent for 30 minutes, the solvent was distilled with an evaporator, followed by vacuum drying.

(2) Preparation of Composite Material

Each additive prepared as above was dispersed in a matrix material to prepare composite materials of samples A1 to A16 and samples B1 to B8. The matrix material constituting each composite material was a cured product of the following two-part epoxy resin.

Epoxy base resin: glycidyl ether of bisphenol A ("jER828" manufactured by Mitsubishi Chemical Corporation; epoxy equivalent: 190 g/eq.)

Epoxy curing agent: amine type ("ST12" manufactured by Mitsubishi Chemical Corporation; amine value: 345 to 385 KOH mg/g)

The various additives, the epoxy main resin, and the epoxy curing agent were mixed at room temperature in an agate mortar at mass ratios shown in Table 1 later, and deformed under vacuum at room temperature for 1 minute. Then, the mixture was heated at 100° C. for 10 minutes with a hot press molding machine and cured. For samples A1 to A16, partial change in particle shape of each additive was visually observed during heating at 100° C. It is thus considered that the aggregation state (stacking structure) of the organic component contained in the additive was temporarily eliminated during heating.

A resin-cured specimen (10 mm×10 mm×1 mm) was prepared by cutting out a portion, in which no air bubble was visually determined, of the prepared cured body. Samples other than sample B1 were set such that the blending amount per volume of each sample was 30% by volume based on the content (mass %) of each additive shown in Table 1 and the specific gravity of the additive measured in the evaluation test as described below. For sample B1, no additive was added thereto, and resin-cured specimens were prepared from epoxy resin only. In Table 1, among additives listed as other additives, some additives are listed while abbreviations of raw materials are directly used, such as PB and MgCO3. For such additives, the raw material is directly added to the epoxy resin without preparing an additive by mixing an organic component and a metal-containing component.

(3) Evaluation of Additive State and Properties of Composite Material

As typical ones of the additives prepared as above, PB—Mg and PB-MOS were observed using a polarizing microscope to check orientation states of the constituents. At this time, in addition to the prepared additives (PB—Mg and PB-MOS), the metal-containing component (MgCO3 or MOS) and the organic component (PB) as raw materials were each dispersed in liquid paraffin and observed.

Further, PB—Mg was subjected to FT-IR measurement to examine interaction between the organic components. At this time, in addition to the prepared PB—Mg, the raw materials MgCO3 and PB were each measured by the powder attenuated total reflection method (ATR method).

Moreover, specific gravity and thermal conductivity were measured for each resin cured product test piece prepared as a composite material as described above. The specific gravity was measured by a water displacement method. The thermal conductivity was measured by a laser flash method using a thermal conduction device ("LFA447" manufactured by NETZSCH). The thermal conductivity was measured in a direction perpendicular to the surface of the cured resin test piece.

Test Results (1) State of Additive

Figure 3:
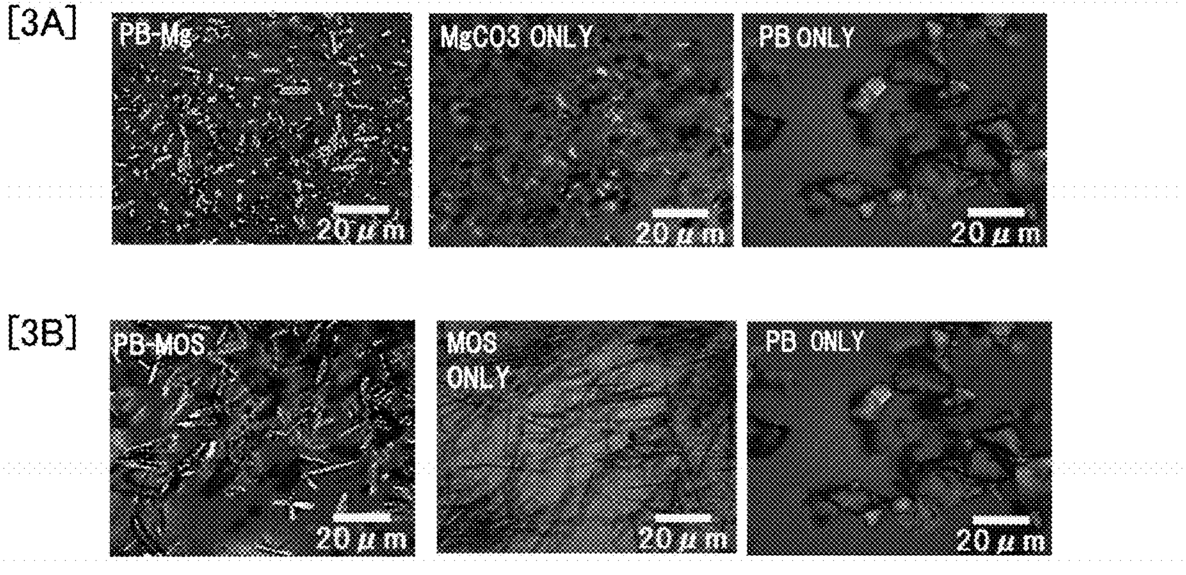
FIGS. 3A and 3B illustrate images, observed by a polarizing microscope, of additives PB—Mg and PB-MOS, respectively, prepared in Example. The respective drawings show, from the left, the observed images on the prepared additives (PB—Mg, PB-MOS), particles of metal-containing components ($MgCO_3$, MOS) being raw materials, and PB being a raw material.

FIGS. 3A and 3B show observation images of the additives PB—Mg and PB-MOS, respectively, by a polarizing microscope. The respective drawings show the observation images of, from the left, the prepared additives (PB—Mg and PB-MOS), the metal compound particles (MgCO3 and MOS) being raw materials, and PB being a raw material. For PB, FIGS. 3A and 3B show the same image. In observation using the polarizing microscope, if a material is oriented in a specific direction, a portion appears in the image so as to be observed brighter than a surrounding region.

In FIG. 3A and FIG. 3B, for the raw material PB, some of grains are observed brighter and are each confirmed to have a certain degree of orientation. With the metal-containing component of the raw material, MgCO3 has a certain degree of orientation as with PB, but for MOS, fibrous particles are observed throughout with an even darkness, suggesting that a crystal structure of the particles does not have high orientation. On the other hand, for the prepared additives, there are particles observed significantly brighter in both PB—Mg in FIG. 3A and PB-MOS in FIG. 3B. Further, a bright area and a dark area sometimes coexist even in a single particle. These results show that the constituent material is oriented in a certain direction with high orientation in each additive. It is considered that each organic component (PB) constituting the additive performs π-π interaction between adjacent molecules, and the organic components are oriented in a direction where they are stacked while the faces of the conjugated π-electron systems are aligned with each other due to the effect of attraction caused by the interaction.

In the PB-MOS image, a size and a shape of the particle each do not change significantly compared with the case of MOS alone, while in the PB—Mg image, the particle is reduced in size and has an anisotropic particle shape compared with the case of MgCO3 alone. For PB-MOS, it is considered that the particle shape of the MOS particle being a raw material does not change in a solvent during manufacturing, and PB coordinates only to a particle surface. On the other hand, for PB—Mg, it is considered that during manufacturing, MgCO3 being a raw material is finely dispersed in a solvent, and a particle shape of the raw material is temporarily eliminated before PB coordinates and PB—Mg particles are newly generated, and thus a size and a shape of the particle are respectively changed from those of the original $MgCO_3$ material. The π-π interaction between the coordinated PB molecules is considered to contribute to the increase in anisotropy of the particle shape. Among the various additives prepared as described above, any additive using MOS as the metal-containing component was formed while the original particle shape was maintained as with PB-MOS. On the other hand, any additive using a metal-containing component other than MOS was formed while the original particle shape was temporarily eliminated before the additive was formed, as with PB—Mg.

Figure 4:
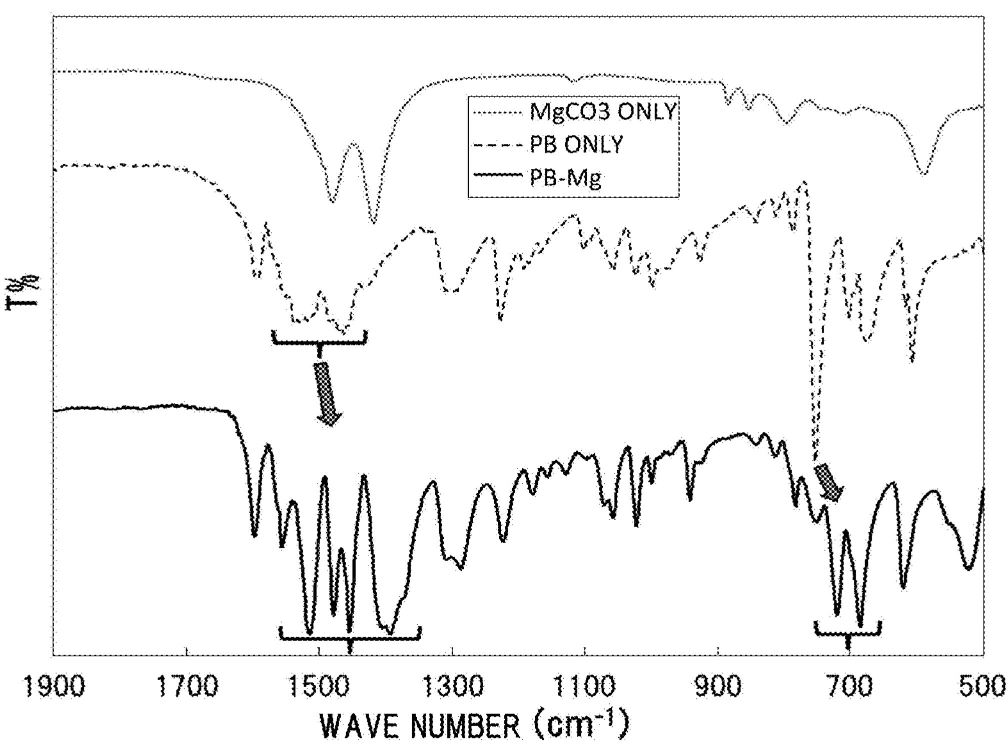
FIG. 4 illustrates a FT-IR spectrum of the additive PB—Mg prepared in the Example. The thick solid line shows a spectrum of the prepared PB—Mg, the dashed line shows a spectrum of the raw material PB, and the thin solid line shows a spectrum of the raw material MgCO3.

FIG. 4 shows FT-IR measurement results for the additive PB—Mg. The thick solid line shows a spectrum of prepared PB—Mg, the dashed line shows a spectrum of raw material PB, and the thin solid line shows a spectrum of raw material MgCO3, where the horizontal axis represents wavenumber, and the vertical axis represents transmittance (T). In the spectra of PB and PB—Mg, there are observed absorption peaks corresponding to C═C stretching vibration in the region 1550 to 1400 $cm^{-1}$ and C═C—H out-of-plane bending vibration in the region 760 to 680 $cm^{-1}$. However, as indicated by arrows in the drawing, each peak is shifted to a lower wavenumber side in PB—Mg compared with PB. Such peak shifts suggest that π-π interaction occurs between stacked molecules adjacent to each other in the aromatic ring in PB. In particular, the lower wavenumber shift of the C═C—H out-of-plane bending vibration can be associated with the phenomenon where the out-of-plane vibration of the aromatic ring is restricted by intermolecular interactions.

(2) Properties of Composite Material

Table 1 summarizes compositions and property measurement results for the composite materials of the samples A1 to A16 and the samples B1 to B8. The upper part shows blending ratios (mass %) of the additives and the matrix materials, and also shows the additive blending amount (vol %). The lower part summarizes the measurement results of specific gravity and thermal conductivity. The left column of the table shows measured specific gravity of each additive.

TABLE 1

| | | Specific | Sample number | | | | | | | | | | | |
|---|---|---|---|---|---|---|---|---|---|---|---|---|---|---|
| | | gravity | A1 | A2 | A3 | A4 | A5 | A6 | A7 | A8 | A9 | A10 | A11 | A12 |
| Thermally conductive additive | PB-Ca | 1.41 | 34 | | | | | | | | | | | |
| | PB-Al | 1.48 | | 35 | | | | | | | | | | |
| | PB-Mg | 1.45 | | | 35 | | | | | | | | | |
| | PB-Zn | 1.58 | | | | 37 | | | | | | | | |
| | PB-MOS | 1.46 | | | | | 35 | | | | | | | |
| | DPP-Al | 1.16 | | | | | | 30 | | | | | | |
| | DPP-Mg | 1.17 | | | | | | | 30 | | | | | |
| | DPP-MOS | 1.18 | | | | | | | | 30 | | | | |
| | BMPP-Mg | 1.56 | | | | | | | | | 37 | | | |
| | BMPP-MOS | 1.56 | | | | | | | | | | 37 | | |
| | PP-Mg | 1.43 | | | | | | | | | | | 34 | |
| | PP-MOS | 1.44 | | | | | | | | | | | | 34 |
| | HPB-Mg | 1.41 | | | | | | | | | | | | |
| | HPB-MOS | 1.41 | | | | | | | | | | | | |
| | HAN-Mg | 1.49 | | | | | | | | | | | | |
| | HAN-MOS | 1.47 | | | | | | | | | | | | |
| Other additives | PB | 1.09 | | | | | | | | | | | | |
| | DPP | 0.80 | | | | | | | | | | | | |
| | MgCO3 | 2.36 | | | | | | | | | | | | |
| | MOS | 2.23 | | | | | | | | | | | | |
| | AA-Mg | 1.40 | | | | | | | | | | | | |
| | AA-MOS | 1.36 | | | | | | | | | | | | |
| Epoxy base resin | | 1.20 | 44 | 43 | 43 | 42 | 43 | 47 | 47 | 47 | 42 | 42 | 44 | 44 |
| Epoxy curing agent | | | 22 | 22 | 22 | 21 | 22 | 23 | 23 | 23 | 21 | 21 | 22 | 22 |
| Additive blending amount (vol %) | | | 30 | 30 | 30 | 30 | 30 | 30 | 30 | 30 | 30 | 30 | 30 | 30 |
| Specific gravity | | | 1.24 | 1.26 | 1.25 | 1.29 | 1.26 | 1.17 | 1.17 | 1.17 | 1.29 | 1.29 | 1.25 | 1.25 |
| Thermal conductivity (W/m · K) | | | 0.40 | 0.39 | 0.43 | 0.39 | 0.51 | 0.40 | 0.46 | 0.64 | 0.41 | 0.50 | 0.43 | 0.52 |

TABLE 1-continued

| | | Specific | Sample number | | | | | | | | | | | |
|---|---|---|---|---|---|---|---|---|---|---|---|---|---|---|
| | | gravity | A13 | A14 | A15 | A16 | B1 | B2 | B3 | B4 | B5 | B6 | B7 | B8 |
| Thermally conductive additive | PB-Ca | 1.41 | | | | | | | | | | | | |
| | PB-Al | 1.48 | | | | | | | | | | | | |
| | PB-Mg | 1.45 | | | | | | | | | | | | |
| | PB-Zn | 1.58 | | | | | | | | | | | | |
| | PB-MOS | 1.46 | | | | | | | | | | | | |
| | DPP-Al | 1.16 | | | | | | | | | | | | |
| | DPP-Mg | 1.17 | | | | | | | | | | | | |
| | DPP-MOS | 1.18 | | | | | | | | | | | | |
| | BMPP-Mg | 1.56 | | | | | | | | | | | | |
| | BMPP-MOS | 1.56 | | | | | | | | | | | | |
| | PP-Mg | 1.43 | | | | | | | | | | | | |
| | PP-MOS | 1.44 | | | | | | | | | | | | |
| | HPB-Mg | 1.41 | 34 | | | | | | | | | | | |
| | HPB-MOS | 1.41 | | 34 | | | | | | | | | | |
| | HAN-Mg | 1.49 | | | 35 | | | | | | | | | |
| | HAN-MOS | 1.47 | | | | 35 | | | | | | | | |
| Other additives | PB | 1.09 | | | | | | 29 | | | | | | 27 |
| | DPP | 0.80 | | | | | | | 23 | | | | | |
| | MgCO3 | 2.36 | | | | | | | | 46 | | | | 8 |
| | MOS | 2.23 | | | | | | | | | 45 | | | |
| | AA-Mg | 1.40 | | | | | | | | | | 34 | | |
| | AA-MOS | 1.36 | | | | | | | | | | | 33 | |
| Epoxy base resin | | 1.20 | 44 | 44 | 43 | 43 | 67 | 48 | 51 | 36 | 37 | 44 | 44 | 43 |
| Epoxy curing agent | | | 22 | 22 | 22 | 22 | 33 | 24 | 26 | 18 | 18 | 22 | 23 | 22 |
| Additive blending amount (vol %) | | | 30 | 30 | 30 | 30 | 0 | 30 | 30 | 3 | 30 | 30 | 30 | 30 |
| Specific gravity | | | 1.27 | 1.24 | 1.27 | 1.26 | 1.20 | 1.15 | 1.06 | 1.53 | 1.49 | 1.24 | 1.23 | 1.25 |
| Thermal conductivity (W/m · K) | | | 0.46 | 0.57 | 0.49 | 0.60 | 0.18 | 0.17 | 0.17 | 0.21 | 0.23 | 0.24 | 0.23 | 0.21 |

In each of the samples A1 to A16, an additive, which is prepared from a metal-containing component and an organic component having a coordination part and a conjugated π-electron system, is added to the matrix material. In any sample, the thermal conductivity is more than twice that of the sample B1 to which no additive is added, and a good thermal conductivity improvement effect is provided by adding the additive. If the thermal conductivity is approximately doubled by the addition of the additive, the thermally conductive additive can be practically sufficiently useful. The improvement in thermal conductivity can be interpreted as a result of the following fact: the organic component coordinates to the metal constituting the metal-containing component to form a coordination complex, and π-π interaction occurs between the conjugated π-electron systems of the neighboring complexes, and the coordination complexes accordingly orientate into a stacking shape. This is consistent with the analysis results of the additive state using a polarizing microscope and FT-IR as described above.

Further, in the samples A1 to A16, the specific gravity of the composite material is reduced to equal to or less than 1.1 times that of the sample B1. This is because a small amount of the additive is added, and the additive includes not only the metal-containing component with a high specific gravity but also the organic component with a low specific gravity. In this way, the thermally conductive additive including the predetermined organic component and metal-containing component provides a high thermal conductivity improvement effect without greatly increasing specific gravity of a relevant material.

Comparing the measurement results of the thermal conductivity of the samples A1 to A16 with each other, for the samples A5, A8, A10, A12, A14, and A16, the thermal conductivity is 0.50 W/(mK) or more, that is, equal to or more than 2.8 times that of the sample B1, and higher than that of any other sample. In any of these samples, the additive used includes MOS as the metal-containing component. This is presumably because MOS itself is a metallic compound with high thermal conductivity, and for MOS, unlike other metal-containing components, the organic component coordinates to the surface while maintaining its fibrous particle shape, leading to excellent orientation and excellent continuity of orientation of the organic component.

The samples B2 to B8 are now considered. In the samples B2 and B3, no metal-containing component is used, and the organic component is added alone to the matrix material. In these samples, thermal conductivity is not improved compared with the sample B1. In other words, even the organic component with the conjugated π-electron system cannot provide the thermal conductivity improvement effect based on the intermolecular interaction and molecular orientation only by simply dispersing the organic component in the matrix material. This suggests the following: In order for an organic component having a conjugated π-electron system to exert a thermal conductivity improvement effect, it is necessary that the organic component coordinates to the metal atom of the metal-containing component to forma coordination complex, and in a state where the coordination complexes are aggregated, adjacent organic components have regular relative positions and are sufficiently close to each other. Thus, the π-π interaction acts between the conjugated π-electron systems of the organic components, and the orientation can be aligned.

In the samples B4 and B5, the organic component is not used, and the metal-containing component is added alone to the matrix material. In these samples, thermal conductivity is increased compared with the sample B1, but a value of the increase is small, approximately 1.2 to 1.3 times higher than that in the sample B1. In other words, the thermal conductivity improvement effect is limited only by simply dispersing the metal-containing component in the matrix material. The particles of the metal-containing component can act as a thermally conductive filler and provide some thermal conductivity improvement effect. To provide a high thermal conductivity improvement effect, however, adjacent particles need to be in contact with each other to form a heat conduction path. The adding amount of 30% by volume adopted herein is insufficient to form the heat conduction path. In addition, if the adding amount of the metal-containing component is increased, a high thermal conductivity improvement effect may be provided, but in such a case, the specific gravity of the composite material may increase, and properties thereof may be deteriorated. On the other hand, in the samples A1 to A16, a high thermal conductivity improvement effect is provided even with the adding amount of 30% by volume as with the samples B4 and B5. From the comparison with the samples B4 and B5, in samples A1 to A16, the metal-containing component does not simply function as a thermally conductive filler, but the organic component coordinated to the metal-containing component dominantly contributes to the thermal conductivity improvement effect.

In the samples B6 and B7, acetylacetone (AA) is used as the organic component constituting the additive. Acetylacetone has no functional group having the conjugated π-electron system. In each of the samples, the measured thermal conductivity is higher than that of the sample B1, but is at most approximately 1.3 times higher than that of the sample B1, the value of which is approximately the same as in the case of the sample B4 or B5 with no organic component. In other words, the samples B6 and B7 are very limited in the effect of improving the thermal conductivity due to using the additive in which the organic component is coordinated to the metal-containing component. This is considered to be because since the organic component has no conjugated π-electron system, even if the coordination complex is formed, strong attractive interaction is not exhibited between neighboring complexes, and thus the effect of improving the thermal conductivity due to the orientation associated with the interaction is substantially not provided. In other words, the organic component to be coordinated to the metal-containing component importantly has a conjugated π-electron system to improve the thermal conductivity.

In the sample B8, the organic component PB and the metal-containing component MgCO3 are independently added to the matrix material. The sample B8 contains PB and $MgCO_3$, the amount of each of which is the same as that in the sample A3, but while the sample A3 shows a thermal conductivity 2.4 times higher than that of the sample B1, the sample B8 shows a thermal conductivity only 1.2 times higher than that. In the sample A3, the organic component and the metal-containing component are mixed in advance to form the thermally conductive additive containing the coordination complex before being added to the matrix material, while such a coordination complex is not formed in the sample B8. This suggests the following. That is, a significant effect of improving the thermal conductivity is not achieved only by coexistence of the organic component having the conjugated π-electron system and the metal-containing component in the matrix material, and it is important for improving the thermal conductivity that the two components form a coordination complex, and π-π interaction and resultant orientation are formed between the coordination complexes.

LIST OF REFERENCE SIGNS

5 Wire harness
51 Insulated wire
52 Connector
53 Tape

The invention claimed is:

1. A thermally conductive additive, comprising:
an organic component; and
a metal-containing component,
wherein the organic component is configured as an organic compound including:
a coordination part capable of multidentate-coordinating to a metal; and
at least one functional group bonded to the coordination part and having a conjugated π-electron system, and
the organic component coordinates in the coordination part to a metal atom constituting the metal-containing component to form a coordination complex,
wherein the metal-containing component forms a continuum in a solid state, and only some of the metal atoms constituting the continuum are coordinated with the organic component, and
wherein the thermally conductive additive achieves high thermal conductivity through formation of a thermal conduction path based on the molecular orientation and stacking by the π-π interaction between the molecules and through suppression of phonon scattering.

2. The thermally conductive additive according to claim 1, wherein the organic component of the coordination complex interacts at the functional group having the conjugated π-electron system with the organic component of another neighboring complex.

3. The thermally conductive additive according to claim 1, wherein the functional group having the conjugated π-electron system contains an aromatic ring or a condensed aromatic ring system.

4. The thermally conductive additive according to claim 3, wherein the functional group having the conjugated π-electron system contains only one aromatic ring or condensed aromatic ring system.

5. The thermally conductive additive according to claim 1, wherein the organic component comprises, in addition to the functional group having the conjugated π-electron system, at least one hydrocarbon group or alkoxy group, having 1 to 8 carbon atoms and having no conjugated π-electron system.

6. The thermally conductive additive according to claim 1, wherein the coordination part has a β-diketone structure.

7. The thermally conductive additive according to claim 6, wherein the organic component has a structure represented by formula (A):

(A)

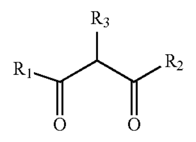

where $R_1$ and $R_2$ are each independently a functional group having a conjugated π-electron system, or a hydrocarbon group or alkoxy group having 1 to 8 carbon atoms and having no conjugated π-electron system, and $R_3$ is a functional group having a conjugated π-electron system, a hydrocarbon group or an alkoxy group having 1 to 8 carbon atoms and having no conjugated π-electron system, or a hydrogen atom, and at least one of the groups $R_1$, $R_2$, and $R_3$ is a functional group having a conjugated π-electron system, where at least two of the groups $R_1$, $R_2$, and $R_3$ may be connected to each other via a ring structure.

8. The thermally conductive additive according to claim 1, wherein the metal-containing component is configured as a fibrous metal compound.

9. A thermally conductive composite material, comprising:

the thermally conductive additive according to claim 1; and a matrix material, wherein the thermally conductive additive is dispersed in the matrix material.

10. The thermally conductive composite material according to claim 9, wherein the matrix material comprises an organic polymer.

11. A wire harness, comprising the thermally conductive composite material according to claim 9.

12. A thermally conductive additive, comprising:

an organic component; and a metal-containing component, wherein the organic component is configured as an organic compound including:

a coordination part capable of multidentate-coordinating to a metal; and at least one functional group bonded to the coordination part and having a conjugated π-electron system, and the organic component coordinates in the coordination part to a metal atom constituting the metal-containing component to form a coordination complex, wherein the organic component coordinates only to the metal atoms occupying the surface of the continuum and the vicinity of the surface, while the organic component does not coordinate to metal atoms occupying the inner region of the continuum, wherein the coordination part has a β-diketone structure, and wherein the organic component has a structure represented by formula (A):

(A)

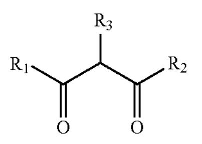

where $R_1$ and $R_2$ are each independently a functional group having a conjugated π-electron system, or a hydrocarbon group or alkoxy group having 1 to 8 carbon atoms and having no conjugated π-electron system, and $R_3$ is a functional group having a conjugated π-electron system, a hydrocarbon group or an alkoxy group having 1 to 8 carbon atoms and having no conjugated π-electron system, or a hydrogen atom, and at least one of the groups $R_1$, $R_2$, and $R_3$ is a functional group having a conjugated π-electron system, where at least two of the groups $R_1$, $R_2$, and $R_3$ may be connected to each other via a ring structure.

13. A thermally conductive additive, comprising:

an organic component; and a metal-containing component, wherein the organic component is configured as an organic compound including:

a coordination part capable of multidentate-coordinating to a metal; and at least one functional group bonded to the coordination part and having a conjugated π-electron system, and the organic component coordinates in the coordination part to a metal atom constituting the metal-containing component to form a coordination complex, wherein the metal-containing component forms a continuum in a solid state, and only some of the metal atoms constituting the continuum are coordinated with the organic component, wherein the coordination part has a β-diketone structure, and wherein the organic component has a structure represented by formula (A):

(A)

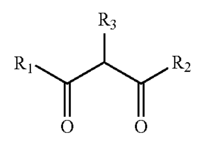

where $R_1$ and $R_2$ are each independently a functional group having a conjugated π-electron system, or a hydrocarbon group or alkoxy group having 1 to 8 carbon atoms and having no conjugated π-electron system, and $R_3$ is a functional group having a conjugated π-electron system, a hydrocarbon group or an alkoxy group having 1 to 8 carbon atoms and having no conjugated n-electron system, or a hydrogen atom, and at least one of the groups $R_1$, $R_2$, and $R_3$ is a functional group having a conjugated π-electron system, where at least two of the groups $R_1$, $R_2$, and $R_3$ may be connected to each other via a ring structure.

* * * * *